United States Patent
Marrs

(12) 
(10) Patent No.: US 6,324,785 B1
(45) Date of Patent: Dec. 4, 2001

(54) PROCESS FOR HARVESTING ORGANIC COMPOUNDS FROM PLANT ROOTS

(75) Inventor: Barry L. Marrs, Kennett Square, PA (US)

(73) Assignee: PharmaLeads, Inc., Newark, DE (US)

( * ) Notice: Subject to any disclaimer, the term of this patent is extended or adjusted under 35 U.S.C. 154(b) by 0 days.

(21) Appl. No.: 09/351,244

(22) Filed: Jul. 12, 1999

(51) Int. Cl.⁷ .......................... A01B 79/00; A01B 79/02; A01C 1/00; A01G 1/00; A01H 3/00
(52) U.S. Cl. ............................ 47/58.1; 504/115; 504/136
(58) Field of Search .............................. 47/58.1; 504/115, 504/136

(56) References Cited

U.S. PATENT DOCUMENTS 5,817,600 * 10/1998 Carstairs et al. ..................... 504/115

OTHER PUBLICATIONS

Dayan et al.; Studies on the Mucilaginous Layer of Barley (*Hordeum vulgare*) Roots; Plant and Soil, vol. 47 No. 1, pp. 171–191, 1977.*

* cited by examiner

*Primary Examiner*—Bruce R. Campell
*Assistant Examiner*—Kent L. Bell
(74) *Attorney, Agent, or Firm*—W. S. Alexander

(57) ABSTRACT

Organic compounds are recovered from the roots of living plants by treating said roots by an extraction with enzymes. The plant is removed from its growing medium, subjected to the extraction and then returned to its original growing medium. The process is thus nondestructive and the plant can be subjected to the enzyme treatment again when it has regenerate the compounds that have been removed. A preferred growing medium is a hydroponic medium. The method has especial utility for providing lead compounds to the pharmaceutical research industry.

23 Claims, No Drawings

PROCESS FOR HARVESTING ORGANIC COMPOUNDS FROM PLANT ROOTS

This invention relates to a novel, non-destructive technique for separation of organic compounds from the roots of plants

BACKGROUND OF THE INVENTION

In recent years, it has been found that there are many organic compounds produced in nature that are as yet completely unknown to man. Researchers in various fields have an interest in isolating and characterizing such compounds and determining whether they have utility in particular areas of interest.

One particularly rich source of organic compounds of this type is the roots of plants. Both herbaceous and woody plants generate organic compounds in their roots. These compounds, often referred to as bioactive phytochemicals, perform a number of functions on behalf of the plant. These functions are primarily protective of the plant against threats such as, inter alia, bacteria, fungi, other plants and insects. The nature of the chemicals produced by a particular plant reflects not only the identity of the plant, but, to a great degree, the environment to which that plant is adapted.

In the natural functioning of the plant, bioactive phytochemicals are contained both within the body of the root and in a mucilaginous sheath formed about the exterior of the root. The nature of the mucilaginous sheath is not completely known, but is believed to be made up of hydrated polysaccharides and mucopolysaccharides. In fact, the great significance of the mucilaginous sheath with respect to the functioning of the bioactive phytochemicals has only recently been realized.

Interest in such compounds is particularly strong in the pharmaceuticals field. Pharmaceutical researchers are especially interested, not only for the possible pharmaceutical activity of such compounds per se, but also for their possible utility as lead compounds for derivatization into other pharmacologically active forms. A substantial amount of effort has been applied to finding and recovering these organic compounds from nature for study.

Presently practiced techniques for recovering organic compounds from plant roots generally involve removing the roots from the remainder of the plant, reducing the roots to a smaller particle size and subjecting the small particle residue to a standard extraction process using conventional organic solvents. This technique, although it is effective in recovering the desired materials, has several drawbacks.

One serious drawback of currently practiced techniques is that the plant is completely destroyed in the process. This is an economic drawback since it now becomes necessary to replace the plant, which can only be done by growing another plant—a time-consuming and sometimes uncertain undertaking. Further, some of the plants that are used are somewhat rare and it is environmentally undesirable for them to be destroyed.

Another drawback of the current process is that, since the process involves solvent extraction, it may be necessary to employ more than one solvent in order to extract all the species present in a candidate plant root system. This can be a problem if the solvents being used are not compatible or if they otherwise require the extraction process to be carried out in more than one step.

It is the object of this invention to provide a novel and improved technique for separating organic compounds from the roots of plants. It is a particular objective of the invention to provide a technique for separating organic compounds from the roots and from the mucilaginous sheath associated with the roots of plants without destroying the plant from which the compounds are removed.

In accordance with this invention, it has been found that when a plant root system with the mucilaginous sheath surrounding the said root system intact or substantially intact, is placed in an aqueous medium containing an enzyme or a mixture of enzymes, the mucilaginous sheath is attacked by the enzyme(s) and the organic compounds within the sheath are liberated into the aqueous medium.

BRIEF DESCRIPTION OF THE INVENTION

The invention to be described herein is a process for separating organic compounds from the root system of a plant, which process comprises immersing the root system of the plant, having the mucilaginous sheath surrounding said root system intact or substantially intact, in an aqueous medium containing one or more enzymes under conditions sufficient to break down the mucilaginous sheath, whereby organic compounds contained within the sheath are liberated into the aqueous medium.

DETAILED DESCRIPTION OF THE INVENTION

One of the advantages of the invention, as stated above, is that it can be carried out in a non-destructive manner. That is to say, it is not necessary to treat the plant in such a way that it is destroyed in the course of removing the desired organic compounds therefrom as is the case with presently known bioactive phytochemical separation techniques. The root system of the plant can be placed in the aqueous medium for the enzyme treatment and, following the enzyme treatment, the plant can be replaced in its growth medium. The mucilaginous sheath is rapidly regrown, usually within a matter of days, and the plant can be subjected to the enzyme treatment again.

The invention will be described with particular emphasis on its application to herbaceous plants but it will be understood that it can also be applied to woody plants as well.

A plant to be used in the practice of the invention can be grown in any medium in which plants are normally grown and to which the specific plant under consideration is amenable to growth. Thus it can be grown, e.g., hydroponically or aeroponically or in dirt or in potting soil mixtures. Any plant found in nature can thus be a candidate for use in the process since all plants generate specific compounds to perform necessary protective functions against specific agents from which protection is required.

In the practice of the invention, it is preferred that the plant be grown either hydroponically or aeroponically. Most preferably, the plant will be grown hydroponically. If the plants is grown in a medium that is neither aeroponic nor hydroponic, ie., in a solid medium, it is necessary to clean all or substantially all of the growing medium from the root system prior to immersion in the aqueous enzyme containing-medium. This can be done by rinsing, but an extra handling step is thus required. Any extra handling step increases the likelihood of damaging the plant so that it cannot be returned to its growing medium for continued growth and reuse. Moreover, when a plant is returned to a solid growing medium, its resumption of growth is much slower and less certain than when it is returned to an aeroponic or hydroponic environment.

As stated above, the preferred growth medium for plants to be employed in the invention is a hydroponic medium. An aqueous medium for hydroponic cultivation of herbaceous plants typically consists essentially of undistilled tap water containing a water soluble plant food. The specific concentrations of ingredients must be maintained within a range in which the plant will not be damaged. Typically a plant food having a nitrogen/phosphorus/potash composition can be used. The characteristics of the plant food and the concentration of the food in the medium will, of course be determined case-by-case based on consideration of the particular plant being grown.

In a hydroponic growth medium, the plant does not encounter the threats to its well-being that are encountered in nature. Thus, it has little or no stimulus to generate the protective bioactive phytochemicals that are of interest in this invention. In order to simulate the conditions that the plant would have experienced in nature, the hydroponically grown plant is exposed to one or more elicitor compounds prior to the enzyme treatment. These are compounds that can imitate the challenges that the plant might have encountered in nature and thereby stimulate the plant to generate the bioactive phytochemical that would have responded to that threat in nature.

The exposure to the elicitor compound is typically continued for a time of about 1 to 2 days prior to the enzyme treatment. The actual time of the treatment is not critical except that it must be sufficient to cause the plant to secrete a sufficient amount of the bioactive phytochemical to make the process economically practical. One very active elicitor compound is arachidonic acid. Other elicitor compounds are known such as, e.g. chitosan breakdown products, aluminum ion, hydrogen peroxide and U.V. light. Other eliciter compounds for stimulating production of bioactive phytochemicals will be known to those skilled in the art.

The enzymes useful in the practice of the invention can be selected from any of the several classes of enzymes. Any water soluble or water dispersible enzyme can be used. In particular, it is preferred to employ water soluble enzymes from the classes known as hydrolases and lyases. These materials are well known and do not per se form a part of the invention. Examples of hydrolases that can be employed include, by way of example, proteases and carbohydrases such as mannanases, amylases and galacturonases. Examples of the lyases include pectin and pectate lyases.

The enzyme concentration required in the aqueous organic compound separation medium is dependent in part on the specific enzyme being employed, the specific plant root being treated and on the size of that root. The amount of enzyme or enzyme mixture required can readily be determined on a case-by-case basis as experience in carrying out the invention is acquired.

The enzyme treatment can be carried out for a time period of a few minutes to several days. Time of treatment is to some degree dependent on the enzyme concentration in the treatment medium. Accordingly, enzyme concentration can be varied to effect digestion over shorter or longer time periods.

The temperature of treatment is not critical except as the temperature might affect the integrity of the plant roots being treated. Any temperature that matches the temperature activity profile of the enzyme employed and does not harm the root system can be used. Temperatures between about −5° C. and 50° C. can be employed successfully.

The pH at which the invention is carried out is likewise not critical so long as it is such that the plant is not harmed and the enzyme employed is active at the chosen ph level.

The ionic strength of the treatment medium resulting from minerals found in the treatment water and such materials as buffers that may be added thereto is preferably lower than about 1.0 M.

The invention will be exemplified by the following examples.

EXAMPLE 1

Butterfly Weed (*Asclepias tuberosa*) was grown hydroponically from seeds under Sylvania Gro Lux Wide Spectrum fluorescent lights in solution of an all purpose water soluble plant food (Schultz 30/20120 All Purpose Plant Food Plus from A. Y. Schultz Company, St. Louis, Mo. 65043). The plant food was present in a concentration of 2 tsp/2 gallons of water. The plants were grown to a height of about 6 to 8 inches, at which time a plant was removed from the growth solution. The plant's roots were blotted with a tissue to remove most of the growth solution and then placed in a solution of arachidonic acid and the Schultz all purpose plant food (0.75 tsp/2 gal) and placed under the growing lights for another 23 hours. The plant was removed from the arachidonic acid/nutrient solution and placed in 50 ml. of a solution of 0.1 ml of ENZECO® Pectinase AJ (22,000 PGU/ml.) and 0.1 ml of ENZECO® Mannanase L (40,000 MGU/ml.) in 100 ml of Schultz plant food solution and 0.05 M phosphate buffer at pH 6.0. (Both Mannanese L and Pectinase AJ were acquired from Enzyme Development Corporation.) After 21 hours, the aqueous solution was removed for analysis and the plant was returned to a fresh solution of Schultz plant food for continued growth and further use.

The aqueous enzyme solution was analyzed by High Performance Liquid Chromatography (HPLC) at 220 mu and 254 mu. The analysis was performed on a Hewlett Packard HPLC unit with a C-18 column at 1 ml/min flow for 20 minutes with gradient of 30 to 90 methanol and 0.5 M aqueous phosphate buffer at pH 3.5. The injection volume was 25 $\mu$l. The arachidonic acid, Schultz nutrient and enzyme solutions were also analyzed using the same method to establish controls against the possible introduction of UV absorbing compounds from other sources.

The resulting spectra were overlaid electronically and it was found that 43 chemical compounds were present. Of these 43 compounds, 15 were well above background (more than 20 miliabsorbance units). Of these 15, 8 absorbed strongly at both 220 nm and 254 nm, 5 absorbed strongly at 220 nm, but weakly or not at all at 254 nm and one absorbed strongly at 254 nm, but weakly or not at all at 220 nm. The compounds were evenly distributed along the gradient, demonstrating a wide variability in polarity.

EXAMPLE 2

Poppy (*Eschscholtzia californica*) was grown hydroponically from seeds substantially as in Example 1 to a height of 4 to 6 inches. A single plant was treated substantially the same as in Example 1. Twenty six chemical entities were observed by HPLC and these were analyzed in the manner described in Example 1. Of these 26, 14 were significant (more than 20 milliabsorbance units). Of these 14, 7 absorbed strongly at both 220 nm and 254 nm, 7 absorbed strongly at 220 nm but weakly or not at all at 254 nm. The compounds were evenly distributed along the gradient demonstrating a wide variability in polarity.

EXAMPLE 3

Purple Cornflower (*Echinea purpurea*) was grown hydroponically from seeds substantially as in Example 1 to a height of 4 to 6 inches. A single plant was treated substantially the same as in Example 1. The resulting new chemical entities were analyzed in the manner described in Example 1. Thirty five chemical entities were observed. Of these 35, 15 were significant (more than 20 milliabsorbance units). Of these 15, 9 absorbed strongly at both 220 and 254 nm, 6 absorbed strongly at 220 nm but weakly or not at all at 254 nm and 1 absorbed strongly at 254 but weakly or not at all at 220 nm. The compounds were evenly distributed along the gradient demonstrating a wide variability in polarity.

EXAMPLE 4

Teasel (*Dipsacus sylvestrus*) was grown hydroponically from seeds substantially as in Example 1 to a height of 3 to 5 inches. A single plant was treated substantially the same as in Example 1. The resulting new chemical entities were analyzed by HPLC in the manner described in Example 1. Thirty eight chemical entities were observed. Of these 36, 22 were significant (more than 20 milliabsorbance units). Of these 22, 5 absorbed strongly at both 220 and 254 nm, 13 absorbed strongly at 220 mu but weakly or not at all at 254 nm and 4 absorbed strongly at 254 nm but weakly or not at all at 220 nm. The compounds were evenly distributed along the gradient demonstrating a wide variability in polarity.

EXAMPLE 5

Teasel (*Dipsacus sylvestrus*) was grown hydroponically from seeds substantially as in Example 1 to a height of 3 to 5 inches. A single plant was removed from the growth solution, the roots were blotted with tissue to remove most of the growth solution and placed in a 1 mM solution of $AgNO_3$ Schultz' nutrients (0.75 tsp/2 gal) and replaced under the growing lights for 23 hours. The plant was then removed from the growth solution and placed in a solution of 0.5 ml of Pectinase AJ and 0.5 ml of Mannanase L in 50 ml of Schultz plant food solution at 0.04 M phosphate buffer at pH 6.0 for 21 hours. The aqueous solution was removed for analysis and the plant was returned to a fresh solution of nutrients for continued growth and further use.

The resulting chemical entities were analyzed in the same manner as described in Example 1. Thirty one chemical entities were observed. Of these 31, 1 absorbed strongly at both 220 and 254 nm, 8 absorbed strongly at 220 but weakly or not at all at 254 mu and 2 absorbed strongly at 254 but weakly or not at all at 220 nm. The compounds were distributed evenly along the gradient demonstrating a wide variability in polarity.

The purpose of this invention is to provide a process by which organic compounds, which include bioactive phytochemicals, can be separated from the root systems of plants. No attempt is made herein to identify specific compounds present in the enzyme solutions analyzed. Specific compounds can be isolated and recovered from the solutions for testing for their pharmaceutical or other utility by techniques known to the art.

What is claimed is:

1. A process for separating organic compounds from the root system of an intact plant, which process comprises immersing the root system of the plant, having the mucilaginous sheath surrounding said root system intact or substantially intact, in an aqueous medium containing one or more enzymes under conditions sufficient to break down the mucilaginous sheath, whereby organic compounds contained within the sheath are liberated into the aqueous medium.

2. A process according to claim 1 wherein the root system of the plant is exposed to one or more elicitor compounds prior to the enzyme treatment.

3. A process according to claim 2 wherein the one or more enzymes are hydrolases or lyases.

4. A process according to claim 3 wherein the one or more enzymes are hydrolases.

5. A process according to claim 4 wherein the hydrolase is selected from the group consisting of proteases and carbohydrases.

6. A process according to claim 2 wherein the aqueous medium contains a mixture of hydrolases and lyases.

7. A process according to claim 6 wherein the aqueous medium contains a mixture of mannanase and pectinase.

8. A process for separating organic compounds from the root system of an intact hydroponically grown plant, which process comprises immersing the root system of the plant, having the mucilaginous sheath surrounding said root system intact or substantially intact, in an aqueous medium containing one or more enzymes under conditions sufficient to break down the mucilaginous sheath, whereby organic compounds contained within the sheath are liberated into the aqueous medium.

9. A process according to claim 8 wherein the root system of the hydroponically grown plant is exposed to one or more elicitor compounds prior to the enzyme treatment.

10. A process according to claim 9 wherein the one or more enzymes are hydrolases or lyases.

11. A process according to claim 10 wherein the one or more enzymes are hydrolases.

12. A process according to claim 10 wherein the hydrolase is selected from the group consisting of proteases and carbohydrases.

13. A process according to claim 9 wherein the aqueous medium contains a mixture of hydrolases and lyases.

14. A process according to claim 13 wherein the aqueous medium contains a mixture of mannanase and pectinase.

15. A process for separating organic compounds from the root system of an intact living plant which process comprises;

a) growing a plant in a hydroponic or aeroponic medium;

b) immersing the root system of said plant, having the mucilaginous sheath surrounding the roots intact or substantially intact, in an aqueous medium containing one or more enzymes under conditions sufficient to break down the mucilaginous sheath surrounding said roots whereby organic compounds are liberated into the aqueous medium;

c) returning the plant to its growth medium; and d) recovering an aqueous solution containing the liberated organic compounds.

16. A process according to claim 15 wherein the plant is grown in a hydroponic medium.

17. A process according to claim 16 wherein the plant is exposed to one or more elicitor compounds during its growing phase.

18. A process according to claim 17 wherein the one or more enzymes are hydrolases or lyases.

19. A process according to claim 18 wherein the one or more enzymes are hydrolases.

20. A process according to claim 19 wherein the hydrolase is selected from the group consisting of proteases and carbohydrases.

21. A process according to claim 18 wherein the aqueous medium contains a mixture of hydrolases and lyases.

22. A process according to claim 21 wherein the aqueous medium contains a mixture of mannanase and pectinase.

23. A process for separating organic compounds from the root system of a plant, which process comprises immersing the root system of an intact plant, having the mucilaginous sheath surrounding said root system intact or substantially intact, in an aqueous medium containing one or more enzymes under conditions sufficient to break down the mucilaginous sheath, whereby organic compounds contained within the root system are liberated into the aqueous medium.

* * * * *

UNITED STATES PATENT AND TRADEMARK OFFICE
CERTIFICATE OF CORRECTION

PATENT NO.   : 6,324,785 B1
DATED        : December 4, 2001
INVENTOR(S)  : Barry L. Marrs It is certified that error appears in the above-identified patent and that said Letters Patent is hereby corrected as shown below:

<u>Column 4,</u>
Lines 31-32, "0.5M aqueous phosphate buffer" is corrected to read -- 0.05M aqueous phosphate buffer --.

Signed and Sealed this

Tenth Day of December, 2002

JAMES E. ROGAN
*Director of the United States Patent and Trademark Office*

UNITED STATES PATENT AND TRADEMARK OFFICE
CERTIFICATE OF CORRECTION

PATENT NO.    : 6,324,785 B1
DATED         : December 4, 2001
INVENTOR(S)   : Barry L. Marrs It is certified that error appears in the above-identified patent and that said Letters Patent is hereby corrected as shown below:

<u>Column 4,</u>
Lines 31-32, "0.5M aqueous phosphate buffer" is corrected to read -- 0.05M aqueous phosphate buffer --.

Signed and Sealed this

Fourteenth Day of January, 2003

JAMES E. ROGAN
*Director of the United States Patent and Trademark Office*